United States Patent
Mitragotri et al.

(10) Patent No.: US 8,389,582 B2
(45) Date of Patent: Mar. 5, 2013

(54) COMPOSITION FOR SOLUBILIZING TISSUE COMPRISING 3-(DECYL DIMETHYL AMMONIO) PROPANE SULFONATE AND TETRAETHYLENE GLYCOL DODECYL ETHER

(76) Inventors: Samir Mitragotri, Santa Barbara, CA (US); Sumit Paliwal, Goleta, CA (US); Makoto Ogura, Ryugasaki (JP); Russell M. Lebovitz, San Diego, CA (US)

( * ) Notice: Subject to any disclaimer, the term of this patent is extended or adjusted under 35 U.S.C. 154(b) by 89 days.

(21) Appl. No.: 13/095,639

(22) Filed: Apr. 27, 2011

(65) Prior Publication Data

US 2012/0004592 A1 Jan. 5, 2012

Related U.S. Application Data

(63) Continuation-in-part of application No. 12/664,994, filed as application No. PCT/US2008/072384 on Aug. 6, 2008, application No. 13/095,639, which is a continuation-in-part of application No. 13/126,105, filed as application No. PCT/US2010/024010 on Feb. 12, 2010.

(60) Provisional application No. 60/963,773, filed on Aug. 6, 2007, provisional application No. 61/152,585, filed on Feb. 13, 2009.

(51) Int. Cl.
A01N 31/14 (2006.01)
A01N 33/12 (2006.01)
A61N 1/30 (2006.01)
A61B 10/00 (2006.01)

(52) U.S. Cl. ........... 514/723; 514/642; 600/562; 604/20

(58) Field of Classification Search .................. None
See application file for complete search history.

(56) References Cited

U.S. PATENT DOCUMENTS

| | | |
|---|---|---|
| 4,268,613 A | 5/1981 | Okishi |
| 5,398,690 A | 3/1995 | Batten et al. |
| 5,492,126 A | 2/1996 | Hennige et al. |
| 5,696,069 A | 12/1997 | Ito et al. |
| 5,739,432 A | 4/1998 | Sinha |
| 5,804,452 A | 9/1998 | Povonost et al. |
| 5,913,833 A | 6/1999 | Elstrom et al. |
| 6,007,497 A | 12/1999 | Huitema |
| 6,093,551 A | 7/2000 | Raithel et al. |
| 6,328,728 B1 * | 12/2001 | Holladay et al. .............. 604/501 |
| 6,544,211 B1 | 4/2003 | Andrew et al. |
| 6,560,478 B1 | 5/2003 | Alfano et al. |
| 6,589,173 B1 | 7/2003 | Mitragotri |
| 2003/0060818 A1 | 3/2003 | Kannenberg et al. |
| 2003/0143116 A1 | 7/2003 | Zheng et al. |
| 2003/0211520 A1 | 11/2003 | Afar et al. |
| 2004/0151745 A1 | 8/2004 | Zimmer et al. |
| 2005/0164903 A1 | 7/2005 | Ko et al. |
| 2006/0100569 A1 | 5/2006 | McRury et al. |
| 2007/0055181 A1 | 3/2007 | Deem et al. |
| 2007/0055261 A1 | 3/2007 | Relley et al. |
| 2007/0059687 A1 | 3/2007 | Ohno et al. |
| 2007/0173448 A1 | 7/2007 | Shah et al. |
| 2010/0261176 A1 | 10/2010 | Mitragotri et al. |

OTHER PUBLICATIONS

Huang et al., "Separation and measurement of desmosine and isodesmosine in vascular tissue hydrolysates by micellar electrokinetic capillary chromatography with a mixed micelle system", J. Chromatography A 1175 : 294-296 (2007).*
Tutulan-Cunita et al., "Mutational analysis of the yeast multidrug resistance ABC transporter Pdr5p with altered drug specificity", Genes to cells (2005) vol. 10, pp. 409-420.
Pubchem polidocanol (pubchem.ncbi.nlm.nih.gov/summary/summary.cgi?cid=24750&loc=ec_rcs, downloaded Oct. 29, 2012.
Written Opinion and International Search Report of the International Searching Authority from related PCT Application No. PCT/US08/72384.

* cited by examiner

*Primary Examiner* — Sandra Saucier
(74) *Attorney, Agent, or Firm* — Benjamen E. Kern

(57) ABSTRACT

Tissue solubilizing compositions are provided. The compositions comprise 3-(decyl dimethyl ammonio) propane sulfonate and polyethylene glycol dodecyl ether, such as tetraethylene glycol dodecyl ether. The compositions may be useful to solubilize tissue, including skin, mucosal membrane, and other tissue. The compositions may be further useful to preserve and recover analytes contained within the solubilized skin, mucosal membrane, and other tissue.

31 Claims, 12 Drawing Sheets

COMPOSITION FOR SOLUBILIZING TISSUE COMPRISING 3-(DECYL DIMETHYL AMMONIO) PROPANE SULFONATE AND TETRAETHYLENE GLYCOL DODECYL ETHER

CROSS-REFERENCE TO RELATED APPLICATIONS

This application is a continuation-in-part application of U.S. patent application Ser. No. 12/664,994, filed on Jun. 29, 2010 as a U.S. National Stage filing of PCT/US2008/72384, filed on Aug. 6, 2008, which, in turn, claims priority to U.S. Provisional Patent Application Ser. No. 60/963,773, filed on Aug. 6, 2007, and now expired. This application is also a continuation-in-part application of Ser. No. 13/126,105, filed on Apr. 26, 2011 as a U.S. National Stage filing of PCT/US2010/24010, filed on Feb. 12, 2010, which, in turn, claims priority to U.S. Provisional Patent Application Ser. No. 61/152,285, filed on Feb. 13, 2009, and now expired. All of these related applications are incorporated by reference herein in their entireties.

STATEMENT REGARDING FEDERALLY SPONSORED RESEARCH OR DEVELOPMENT

This invention was made with government support under federal grant number W81XWH-06-01-00400 awarded by the United States Army. The United States Government has certain rights in this invention.

BACKGROUND

Skin is the "window" to the body. Skin is unique among the body's organs for several reasons: (1) skin is the largest organ of the human body; (2) skin is directly exposed to the environment; (3) skin is an excellent excretory organ; (4) skin is the most visible and accessible organ of the body; and (5) skin is a highly active immune organ of the body.

Skin has another important quality: The molecular profile of skin has information that is valuable for physiological monitoring of, among other things, small organic molecules, proteins, DNA, RNA, and lipids. Much can be learned from skin's molecular profiling. For example, pathogens (e.g., bacteria) that grow on skin may allow for forensic identification. Skin's molecular profile may reveal environmental factors to which the body has been passively exposed. These environmental factors may range from the mundane, e.g., allergens, toxins, and cosmetic products, to the industrial and/or agricultural, e.g., industrial solvents, fertilizers, and pesticides, to the dangerous, e.g., explosives and other warfare agents.

Skin's molecular profile may also reveal factors to which the body has been actively exposed. More particularly, skin's molecular profile may reveal what the body has consumed. For example, abused substances (e.g., illegal drugs or narcotics) and therapeutic drugs (e.g., tramadol, fluconazole, barbitals, and anabolic steroids) may be found in skin weeks after consumption.

Skin's molecular profile may also aid diagnosis of conditions and diseases. For example, skin cholesterol is a proxy of the extent of arterial blocks. Glycation of skin collagen is an indicator of a history of diabetes. Skin deposition of β-amyloids may indicate the existence and extent of Alzheimer's disease. And skin globular proteins (e.g., IgE) may indicate allergies to specific allergens.

Several methods exist for sampling biomolecules from skin. For example, one current method is skin biopsy. However, skin biopsy is invasive and analysis is difficult. Practically speaking, skin biopsy is designed for well-equipped experts and, thus, its use in a point-of-care setting is limited. Another current method for sampling biomolecules from skin, tape stripping, suffers from these same limitations and is generally unacceptable because of variability in results. Yet another current method for sampling biomolecules from skin is taking a skin swab. While desirable because of its simplicity, a skin swab is superficial in its depth of inspection, and qualitative in its results. Finally, tissue has been subjected to ultrasound in the presence of surfactants such as sorbitans ("SPANs"), polyoxyethelene sorbitans combined with fatty acids (Tween® surfactants), cetyl trimethylammonium bromide ("CTAB"), and their mixtures. See U.S. Pat. No. 6,589,173 issued to Mitragotri et al. However, SPANs, Tween® surfactants, and CTAB, individually and collectively, have been found to be unsuitable to recover skin constituents. Sorbitans and Tween® surfactants, which are nonionic surfactants, are mild and non-denaturing in character, but are ineffective to solubilize skin tissue. CTAB, a cationic surfactant, is effective to solubilize skin tissue, but unsuitably denatures proteins, profoundly changing properties of biomolecules in solution, rendering them unusable for functional purposes.

Along with providing a cornucopia of information, skin and other epithelial surfaces in the body such as mucosal membranes lining the oral cavity, upper and lower respiratory tracts, upper and lower GI tracts, GU tracts, and cornea of the eye, can also be a host to myriad undesirable cosmetic conditions, such as age spots, skin tags, seborrheic keratosis, scar tissues, xanthomas, non-cancerous hyperproliferative conditions, surface bumps, and scaly patches, and therapeutic conditions such as basal cell and squamous carcinoma skin tumors, and actinic keratosis. Similarly mucosal membranes in the body may be host to surface-located therapeutic conditions such as leukoplakia, and surface cancers relating to Barrett's esophagus and right-colon pre-cancer plaque. For these conditions, solubilization and remodeling or removal may be the primary concern, with or without subsequent diagnostic processing.

Thus, a need exists for compositions for skin sampling, as well as for mucosal membrane and other tissue sampling, which, when used in conjunction with applied energy, at least partially solubilize such skin, mucosal membrane, and other tissue. A further need exists to preserve the functionality and structural integrity of analytes, including biomolecules, obtained from the solubilized skin, mucosal membrane, and other tissue. Finally, a related need exists to remove surface lesions from skin and mucosal membranes, while preserving biomolecules obtained from the lesions for diagnosis or prognosis.

SUMMARY

In one embodiment, a composition is provided, the composition comprising: 3-(decyl dimethyl ammonio) propane sulfonate ("DPS"); and polyethylene glycol dodecyl ether. In one embodiment, the polyethylene glycol dodecyl ether comprises tetraethylene glycol dodecyl ether ("B30").

In one embodiment, the composition is exclusive of Tween® surfactants. In one embodiment, the composition is exclusive of cationic surfactants, including CTAB. In one embodiment, the composition is exclusive of SPANs. In one embodiment, the composition is exclusive of sodium alkyl sulfates.

In still another embodiment, a method is provided for solubilizing and remodeling and/or removing tissue on or beneath a patient's skin, comprising applying energy to a region of interest on the skin; and contacting the region with a tissue solubilizing composition.

In another embodiment, a method for recovering analytes from mucosal membrane, skin, or other tissue is provided, the method comprising: applying energy to a region of interest on the mucosal membrane, skin, or other tissue containing at least one analyte; contacting the region with a tissue solubilizing composition, thereby solubilizing at least some of the mucosal membrane, skin, or other tissue containing at least one analyte; and collecting the at least one analyte from the solubilized mucosal membrane, skin, and other tissue.

BRIEF DESCRIPTION OF THE DRAWINGS

In the accompanying figures, experimental data are given that, together with the detailed description provided below, describe example embodiments of the claimed invention.

DETAILED DESCRIPTION

Figure 1:
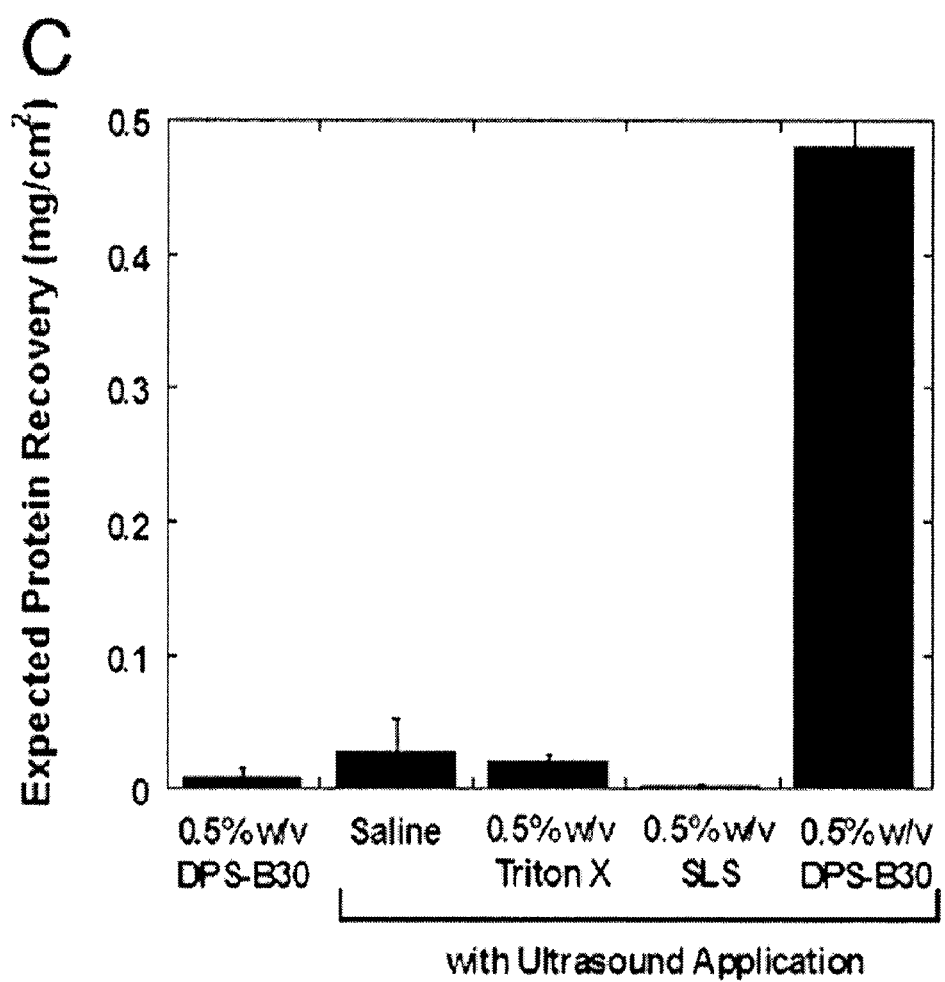
FIG. 1 illustrates a comparison of the expected functional protein recovery using DPS-B30 (0.5% (w/v)) with and without ultrasound application, with the expected functional protein recovery using saline, 0.5% (w/v) sodium lauryl sulfate ("SLS"), and 1% Triton-X-10 with ultrasound application.

In one embodiment, a composition is provided, the composition comprising DPS and polyethylene glycol dodecyl ether. In one embodiment, the polyethylene glycol dodecyl ether comprises B30. DPS is a zwitterionic surfactant. B30 is a nonionic surfactant. The DPS and B30 may be dissolved in a buffer solution. The buffer solution may comprise, for example, one or more of phosphate-buffered saline ("PBS"), tris-buffered saline, tris-hydrochloride, and ethylenediaminetetraacetic acid ("EDTA"). The DPS and B30 may be present in a total concentration of between about 0.01% and about 10% (w/v) in the buffer solution. For example, the DPS and B30 may be present in a total concentration of about 0.01% to about 5% (w/v) in the buffer solution, including total concentrations of about 0.1% (w/v) to about 2% (w/v) in the buffer solution, about 1% (w/v) in the buffer solution, and about 0.1% (w/v) to about 0.5% (w/v) in the buffer solution. In one embodiment, the DPS and B30 are present in a total concentration of about 0.5% (w/v) in the buffer solution. The DPS and B30 may be present in a ratio of 3:2 to 2:3. In one embodiment, the DPS and B30 may be present in a ratio of about 1:1.

In one embodiment, a method is provided for solubilizing and remodeling and/or removing tissue on or beneath a patient's skin, comprising applying energy to a region of interest on the skin; and contacting the region with a tissue solubilizing composition comprising, e.g., DPS and B30.

In another embodiment, a method for recovering analytes from mucosal membrane, skin, or other tissue is provided, the method comprising: applying energy to a region of interest on the mucosal membrane, skin, or other tissue containing at least one analyte; contacting the region with a tissue solubilizing composition, comprising, e.g., DPS and B30, thereby solubilizing at least some of the mucosal membrane, skin, or other tissue containing at least one analyte; and collecting the at least one analyte from the solubilized mucosal membrane, skin, and other tissue.

In some embodiments, the "other tissue" may include breast, prostate, eye, vagina, bladder, nail, hair, colon, testicles, intestine, lung, brain, pancreas, liver, heart, bone, or aorta wall.

In some embodiments, the "analyte" may include any biomolecule, drug, small molecule, warfare agent, environmental contaminant, microbe, and the like that is present in or on the tissue and can be extracted from the tissue of interest.

In some embodiments, the "biomolecules" may include proteins (e.g., disease biomarkers such as cancer biomarkers and antibodies: IgE, IgG, IgA, IgD, or IgM, and the like), peptides, lipids (e.g., cholesterol, ceramides, and fatty acids), nucleic acids (e.g., RNA and DNA), small molecules (e.g., glucose, urea, and creatine), small molecule drugs or metabolites of small molecule drugs, microbes, inorganic molecules, elements, and ions (e.g., iron, $Ca^{2+}$, $K^+$, $Na^+$, and the like). In some embodiments, the biomolecule is exclusive of glucose and cancer markers.

In some embodiments, the "drugs" may include abused drugs, such as, for example, cocaine, heroin, methyl amphetamine, and prescription drugs taken in excess of dosage, or taken without a prescription (e.g., painkillers such as opioids); and therapeutic drugs, such as, for example, tramadol, fluconazole, barbitals, and anabolic steroids.

In some embodiments, the "warfare agents" may include any molecule, compound, or composition of either biological or chemical origin that may be used as a weapon. Non-limiting examples of warfare agents include explosives, nerve gases (e.g., VX and Sarin), phosgene, toxins, spores (e.g., anthrax), and the like.

In some embodiments, the "environmental contaminants" may include any molecule, compound, or composition that can be detrimental to an individual, e.g., when at concentrations elevated above a risk threshold. Examples include water pollutants (e.g., fertilizers, pesticides, fungicides, insecticides, herbicides, heavy metals, and halides), soil pollutants (e.g., fertilizers, pesticides, fungicides, insecticides, herbicides, heavy metals, and halides), and air pollutants (e.g., $NO_x$, $SO_x$, greenhouse gases, persistent organic pollutants, particulate matter, and smog).

In some embodiments, the "energy" may be applied by any number of suitable methods, including mechanical (e.g., abrasion, shear, vacuum, pressure, suction), ultrasound, optical (e.g., laser), thermal, and electrical energy. However, in one embodiment, the energy does not include externally supplied thermal energy (i.e., heat). Suitable energy applicators are disclosed in U.S. patent application Ser. Nos. 12/664,994 and 13/126,105, each of which are incorporated by reference herein in their entireties.

In one embodiment, the compositions described herein may be useful for, among other things, disaggregating, solubilizing, and stabilizing cell components to be used as disease biomarkers, forensic biomarkers, or both. In one embodiment, the compositions are useful to disaggregate, solubilize, and stabilize components from living tissues in situ, from freshly resected tissues, frozen resected tissues, preserved paraffin embedded tissues, tissue and cell extracts and cultured cells derived from cell lines or resected tissues, and from exogenous agents such as viruses, bacteria, and prions.

In one embodiment, the compositions described herein may be useful to solubilize, remodel, and remove diseased tissue on or beneath the surface of the skin, or elsewhere within the body. For example, the composition may be useful to solubilize, remodel, and remove tissue hosting precancerous conditions such as actinic keratosis, leukoplakia, Barretts esophagus, and right-colon pre-cancer plaque, and surface cancers arising from any of these precancerous conditions. Other therapeutic uses may include solubilizing and removing tumors from a variety of surface or deep sites, or treating tumor surgical margins to remove any residual tumor cells at these sites. In some instances, after treating tumors with compositions and solubilizing the constituent tumor markers, the immune system may detect the dissolved tumor markers and initiate a potent anti-tumor immune response against these markers, leading to regression of the local tumor, as well as destruction of any systemic tumor cells carrying the detected tumor markers.

In one embodiment, the compositions described herein may be useful for treating skin lesions and damaged skin with therapeutic molecules and drugs that are unable to penetrate an intact outer skin barrier. More particularly, the compositions described herein may be useful to enhance absorption of topical therapeutics by removing diseased tissue, inflammatory cells, and thickened, hyper-keratinized skin that may block access to otherwise effective topical therapies. An example of such a use is as a pre-treatment for psoriasis topical therapies, since psoriasis lesions typically have a hardened top layer or hyperkeratosis that inhibits absorption. In one embodiment, such treatment may include perturbation of the outer skin barrier using the compositions, and in some circumstances applied energy, to disrupt the barrier by disaggregation and solubilization of barrier cells and tissues, followed by application of the therapeutic molecules and drugs directly to the surface of the barrier-perturbed skin. Example therapeutic molecules and drugs may include, for example, DNA-based drugs, RNA-based drugs, protein-based drugs, peptide-based drugs, lipid-based drugs, carbohydrate-based drugs, small molecule drugs, nanoparticle based drugs, liposome-encapsulated drugs, and combinations of such classes of drugs.

In one embodiment, the compositions described herein may be useful for introducing therapeutic or diagnostic molecules and drugs into the body and bloodstream by disrupting the outer skin layer. In one embodiment, the introducing may include perturbation of the outer skin barrier using the compositions, and in some circumstances applied energy, to disrupt the barrier by disaggregation and solubilization of barrier cells and tissues, followed by application of the therapeutic or diagnostic molecules directly to the surface of the barrier-perturbed skin.

In another embodiment, the compositions described herein may be useful to remove malignant and benign growths and obstructions in other organs in the body or within the central and peripheral nervous systems, including the eye, middle ear, brain, spinal cord, nerve roots, and ganglia. Since the compositions described herein may dissociate and dissolve diseased tissue directly after injection through a thin needle or catheter, the compositions may allow ablative surgery in areas that are not accessible to either open surgery or even to minimally invasive surgical instruments (such as in the vascular system, including arteries and coronary arteries).

In another embodiment, the compositions may be useful to diminish or reduce intra-abdominal and peritoneal adhesions by dissolving specific bands of adherent tissue between intra-abdominal tissues and organs.

In one embodiment, the compositions described herein may be useful for wound debridement. In one embodiment, the treatment may include contacting the compositions, and in some circumstances applied energy, to a wound's surrounding tissue to remove unhealthy tissue, including, for example, necrotic eschar and fibrinous slough.

In one embodiment, the compositions described herein may be useful as a bio-glue to enhance post-operation healing.

In one embodiment, the compositions described herein may be useful to promote oral and dental hygiene. For example, in one embodiment, the compositions may be useful to soften and/or dissolve hard and soft deposits on teeth and dentures.

In one embodiment, the compositions described herein may be useful to solubilize, remodel, and remove cosmetically relevant structures on or beneath the surface of the skin. For example, in one embodiment, the compositions described herein may be useful for treating aged, scarred, and UV-damaged skin, and removing and/or remodeling age spots, skin tags, seborrheic keratosis, scar tissues, xanthomas, non-cancerous hyperproliferative conditions, surface bumps, and scaly patches. In one embodiment, the use may include perturbation of the outer skin barrier using the compositions, and in some circumstances applied energy, to disrupt the barrier by disaggregation and solubilization of barrier cells and tissues. In one embodiment, the compositions may be introduced to deeper layers of skin to facilitate disaggregation, solubilization, and removal of structures associated with wrinkling, scarring, or both, of the skin surface. Other cosmetic uses include dermal peel or skin bleaching. The compositions may be used to remove discoloration of the skin associated with previous injury, UV-damage, or aging. In some embodiments, the perturbation may be followed by application of therapeutic drugs or natural products and other cosmetic compositions that are believed or known to increase the smoothness, elasticity, and resilience of skin. Such cosmetic compositions may include, for example, elastin or its peptides (e.g., V-V-P-Q), collagen or its peptides, resveratrol, idebenone, co-enzyme Q10, acetyl hexapeptide-3, glycosaminoglycans, palmitoyl pentapeptide-4, sodium hyaluronate, and the like, and combinations thereof.

In one embodiment, cell components recovered using the compositions may be introduced into biochemical assays to detect, quantify, and identify specific biomarkers associated with specific diseases. The biochemical assays may include all molecular diagnostic assays for detecting DNA, RNA, proteins, peptides, lipids, carbohydrates, and small molecules, both endogenous and exogenous. The biochemical assays to be used include PCR, ELISA, chromatography, gel analysis, electrophoresis, Western Blots, Southern Blots, Northern Blots, and other methods used in clinical laboratories for identification of molecular biomarkers of disease.

In one embodiment, the compositions described herein may be useful in the treatment of mucosal and skin lesions. Such use may involve impregnating an abrasive and absorbent swab (similar to a for-daily-use facial exfoliating sponge) with one or more of the compositions, and applying the swab to the region of interest with medium pressure in a twisting or back-and-forth motion onto target tissue for a predetermined time. The depth may be controlled by the amount of pressure, as well as application time. After the lesion is dissolved and the released biomarkers are absorbed into the pad, the swab and the dissolved tissue may be collected and sent to, e.g., a pathology lab, for biomarker and other analyte analysis.

Further, the compositions may be useful to treat, as well as solubilize biomarkers for infectious agents relating to, epithelial lesions due to chronic infections, including, for example, warts (virus-induced), molluscum contagiosum (virus induced), and fungal diseases of the skin, nails, hair, and mucous membranes, and any other chronic skin lesion due to a microbiological agent.

The following examples demonstrate that the compositions described herein are useful to dissolve target tissue and preserve biomarkers and other analytes that may be used to diagnose or confirm a diagnosis. This dual activity provides a clear advantage over current methods for dissolving tissue and collecting samples.

EXAMPLES

Certain embodiments are described below in the form of examples. It is impossible to depict every potential application of the invention. Thus, while the embodiments are described in considerable detail, it is not the intention to restrict or in any way limit the scope of the appended claims to such detail, or to any particular embodiment.

Example 1

Protein Bioactivity Retention of DPS-B30

Mouse monoclonal Immunoglobulin E antibody (IgE; Catalog Number: MCA2259, AbD Serotec, Raleigh, N.C.) with functional binding specificity toward chicken albumin (OVA) was used as a model protein to demonstrate the protein bioactivity retention of DPS-B30 (0.5% (w/v)). Specifically, an enzyme-linked immunosorbent assay (ELISA) was performed to determine if IgE antibodies incubated in DPS-B30 retained their functionality to bind OVA specifically.

All ELISA reagents were purchased from KPL (Gaithersburg, Md.). Immulon-2 U-bottom polystyrene plates purchased from Dynex Laboratories (Chantilly, Va.) were coated with 100 µg OVA per well (1 mg/mL) in coating buffer for 1 h at room temperature. The plates were blocked with non-fat milk based blocking solution for 15 min. Test samples were generated by pre-incubating IgE antibody at 1 µg/mL with DBS-B30 for 1 hr, and loading on to the ELISA plate. The plates were incubated for 1 h at room temperature and washed three times with wash buffer. The plates were incubated with horseradish peroxidase-conjugated goat anti-mouse IgE antibody (2 µg/mL; Catalog Number: GE-90P-Z, ICL Inc., Newberg, Oreg.) for 1 h. The plates were washed four times with wash buffer, and treated with ABTS two-component substrate system. The absorbance was read at 405 nm 5 min after mixing of substrate.

The ELISA signal was corrected for non-specific background activity, obtained by omitting addition of IgE antibody. DBS-B30 bioactivity retention was compared with IgE dissolved in PBS as the positive control (100% bioactivity retention). DPS-B30 exhibited greater than 90% bioactivity retention.

Example 2

DPS-B30 Tissue Solubilization

Tissue solubilization was performed with surfactant (DBS-B30 (0.5% (w/v)) dissolution in conjunction with ultrasound. Porcine skin was used as a model tissue. The tightly packed and highly keratinized cellular environment of porcine skin tissue presents a formidable barrier to solubilization and, therefore, provided a suitable platform to perform solubilization studies. Porcine skin was frozen immediately after harvesting and shipped overnight over dry ice from Lampire Biological Laboratories Inc. (Pipersville, Pa.). The skin was stored at −70° C. until the experiment. Two hours before the experiment, skin was thawed at room temperature and cut into small pieces (2.5 cm×2.5 cm). Skin pieces stripped-off from subcutaneous fat and with no visible imperfections such as scratches and abrasions were used.

The solubilization experiment was carried out by mounting the skin piece on a Franz diffusion cell assembly (tissue exposure area of 1.77 $cm^2$; Permegear, Hellertown, Pa.). The receiver chamber of the diffusion cell was filled with PBS and the donor chamber was filled with 1 mL of DPS-B30 as the sampling buffer. DPS-B30 also acted as the coupling fluid between the ultrasound transducer and the tissue. Solubilization was performed at room temperature with a 600-Watt probe sonicator (Sonics & Materials, Newtown, Conn.) operating at a frequency of 20 kHz. The ultrasound transducer was placed at a distance of 5 mm from the tissue surface and an ultrasonic intensity of 2.4 $W/cm^2$ at 50% duty cycle was applied for 3 min. The sampling buffer, now containing solubilized tissue constituents, was aspirated and kept at −70° C. until analysis. The solubilization ability of DPS-B30 was quantified by the concentration of protein. Supernatants were isolated from solubilized skin using a centrifuge operating at 10,000 g and 4° C. for 15 min. Protein concentration of the supernatant was measured by using a colorimetric detection kit (Micro BCA Protein Assay Kit; Pierce, Rockford, Ill.). Protein concentration was determined by dividing the total protein content of the sample by the solubilized tissue area. DPS-B30 achieved protein solubilization of nearly 0.5 $mg/cm^2$.

FIG. 1 compares the expected functional protein recovery of DPS-B30 (0.5% (w/v)) with 0.5% (w/v) SLS, a surfactant commonly combined with ultrasound for transdermal drug delivery applications, and 1% Triton-X-10. Expected functional protein recovery is the product of fractional bioactivity retained and total solubilized protein. In addition to possessing only a moderate solubilization ability (0.07 mg/cm$^2$), SLS is highly denaturing, which results in a low functional protein recovery potential (~0.002 mg/cm$^2$). In contrast, DPS-B30 formulation not only solubilizes more skin proteins (0.48 mg/cm$^2$), but also preserves protein activity, resulting in an excess of 230-fold enhancement in functional protein recovery potential over SLS. Similarly, the ability of 0.5% (w/v) DPS-B30 to harvest functional proteins was more than 25-fold higher over 1% (w/v) Triton X-100.

Example 3

Profiling of Sampled Proteins

DPS-B30 (0.5% (w/v)) was tested for its ability to preserve functionality of various types of proteins under ultrasonic exposure. Proteins (solubilization with 0.5% (w/v) DPS-B30 formulation with in situ 3 min sonication) from porcine skin and mucosal tissues including colon, nasal, and buccal mucosa were characterized. Mucosal tissues were procured from Sierra for Medical Science Inc. (Whittier, Calif.). Tissues were frozen over dry ice immediately after harvesting and stored at −70° C. Sampling was performed by mounting the tissues on a Franz diffusion cell assembly. Tissue homogenate samples were also prepared for comparative analysis. Epidermal skin and mucosal membranes were gently scraped from the bulk tissues using a sharp scalpel and completely homogenized in 0.5% (w/v) DPS-B30 surfactant formulation using a mechanical homogenizer (Tissue Master-240, Omni International, Marietta, Ga.). An ice-bath was used to avoid temperature increase during homogenization. Care was taken to avoid scraping of the muscle and connective tissue underlying the mucosa. One dimensional SDS electrophoresis was performed under reducing conditions with 7.5% polyacrylamide gels (Bio-Rad Laboratories, Hercules, Calif.) and protein samples were adjusted to a final concentration of 2% SDS and 2% mercaptoethanol prior to loading. The protein migration patterns on fixed gels were stained with SYPRO® Ruby Protein Gel Stain reagent (170-3125, Bio-Rad Laboratories, Hercules, Calif.) and digitally imaged.

Figure 2A:
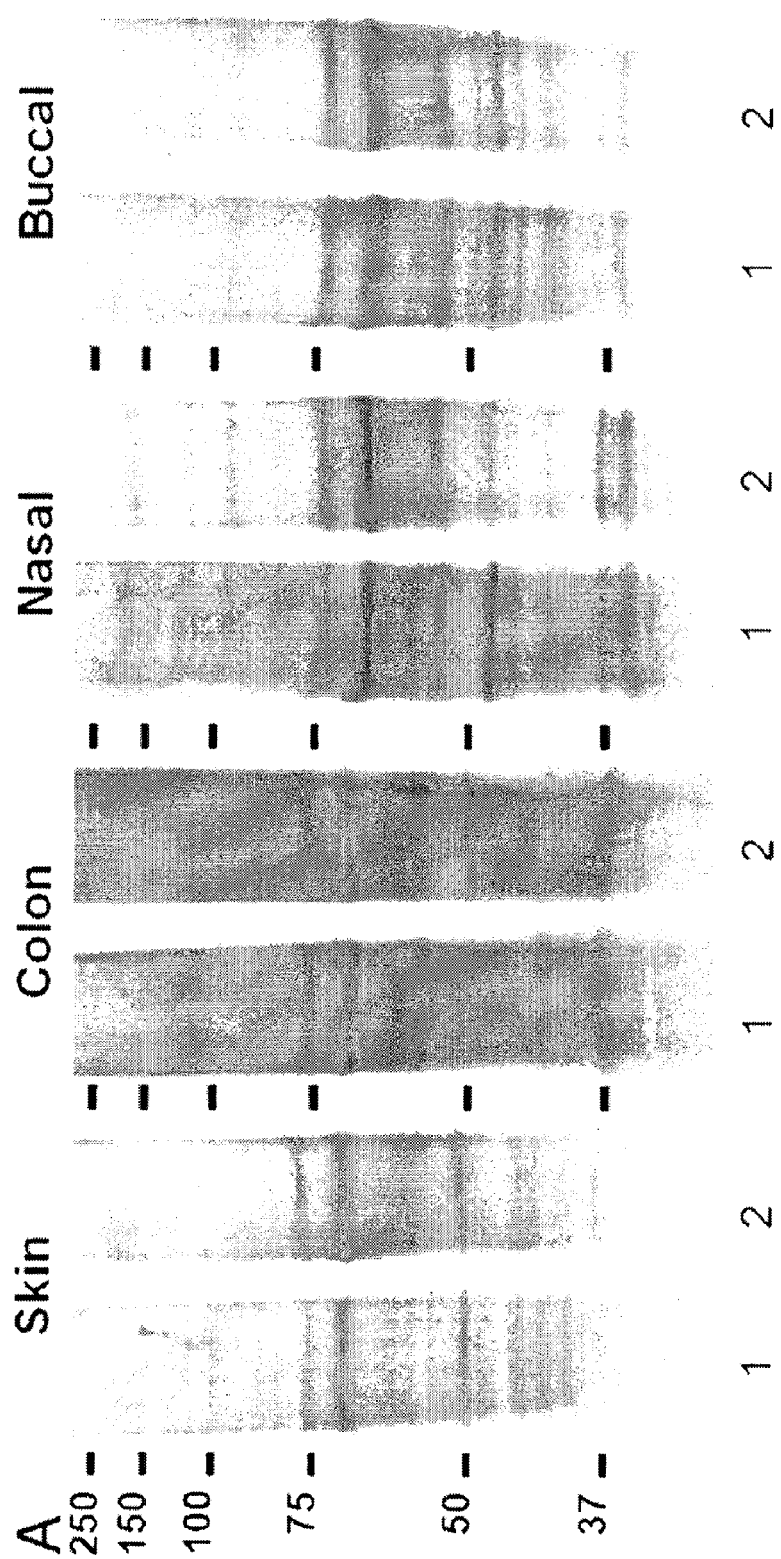
FIG. 2a illustrates a comparison of representative electrophoretic profiles of proteins present in various tissue samples solubilized using DPS-B30 (0.5% (w/v)) and mechanical agitation (lane 2), with profiles existing in respective homogenized skin and mucosal tissues (lane 1).

FIG. 2a illustrates representative electrophoretic profiles of proteins present in various samples (lane 2), which exhibit a high congruence with profiles existing in respective homogenized skin and mucosal tissues (lane 1).

Example 4

Assessment of Protein Bioactivity

A globular protein (IgE) and three enzymes (lactate dehydrogenase (LDH), beta-galactosidase (β-Gal), and lysozyme) were subjected to DPS-B30 (0.5% (w/v)) and sonication, and their bioactivity was monitored over time. In separate experiments, these proteins were added to 5 mL of DPS-B30 and the sample was transferred to a sonication chamber (centrifuge tube #430290, Corning Inc., Corning, N.Y.). Solubilization was performed at room temperature with a 600-Watt probe sonicator (Sonics & Materials, Newtown, Conn.) operating at a frequency of 20 kHz. The ultrasound transducer was placed at a distance of 5 mm from the tissue surface and an ultrasonic intensity of 2.4 W/cm$^2$ at 50% duty cycle was applied for 3 minutes. Proteins dissolved in PBS were prepared as comparative controls. Ultrasound (20 kHz, 2.4 W/cm$^2$, 50% duty cycle) was exposed for up to 6 min by lowering the probe transducer to a distance of 5 mm from the bottom of the chamber. 100 μL samples were periodically collected for analyzing protein bioactivity during ultrasound exposure. IgE functionality was assessed using the ELISA protocol described above; however, a more sensitive chemiluminescent substrate (LumiGLO; KPL, Gaithersburg, Md.) was used. LDH enzymatic activity was measured using a colorimetric assay kit according to manufacturer's guidelines (Catalog Number: G1780; Promega Corp., Fitchburg, Wis.). β-Gal enzymatic activity was also measured using a colorimetric assay kit according to manufacturer's guidelines (Catalog Number: 72134; Anaspec Inc., Fremont, Calif.). Samples were prepared at an initial concentration of 100 ng/mL IgE (MCA2259, AbD Serotec, Raleigh, N.C.), 1:500 dilution of LDH stock provided in the assay kit, 10 μg/mL β-Gal (G5635; Sigma Aldrich, St. Louis, Mo.), and 300 U/mL lysozome (L6876; Sigma Aldrich).

Figure 2B:
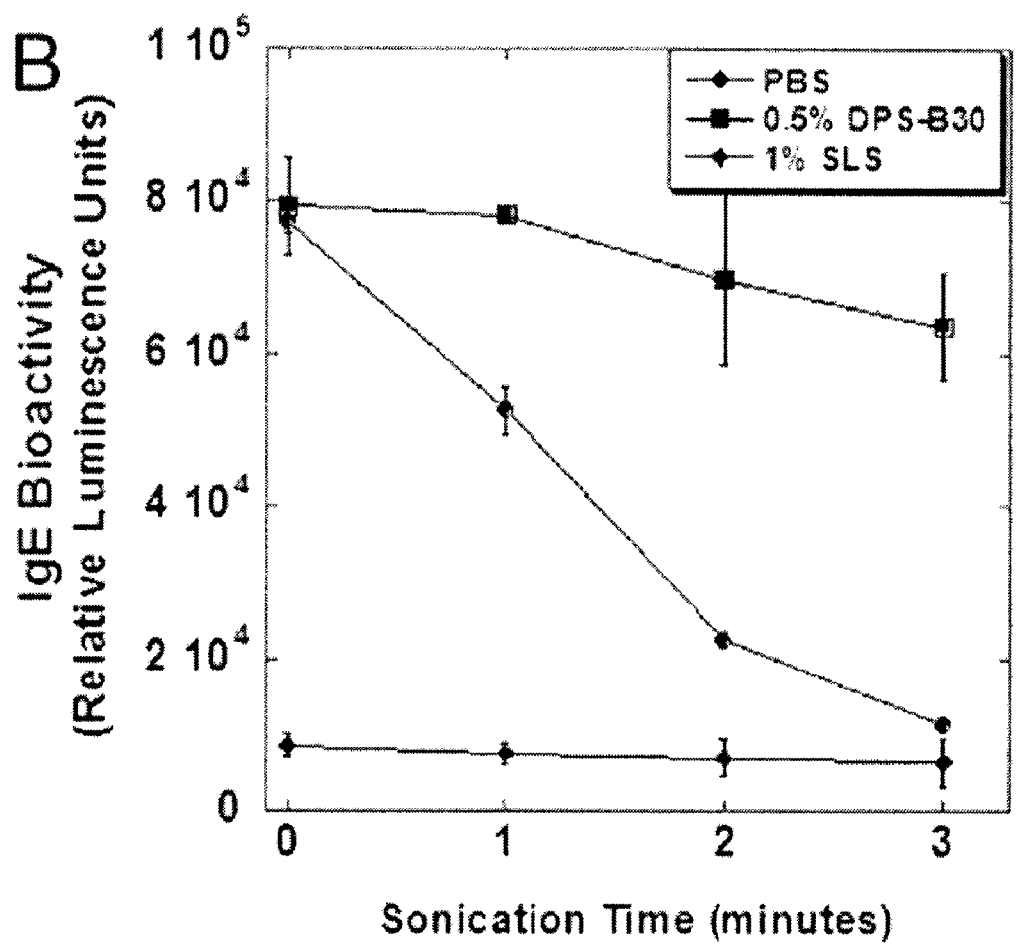
FIG. 2b illustrates a comparison of the effect on bioactivity of IgE proteins when the proteins were subjected to ultrasonic denaturing stress in various solubilizing compositions.

As shown in FIG. 2b, IgE remained functionally viable during the sampling procedure. The DPS-B30 formulation protected IgE proteins against ultrasonic denaturing stress. In contrast, a progressively sharp decrease in bioactivity was observed for IgE proteins prepared in PBS. Similarly, IgE prepared in SLS showed a complete state of denaturation.

Figure 2C:
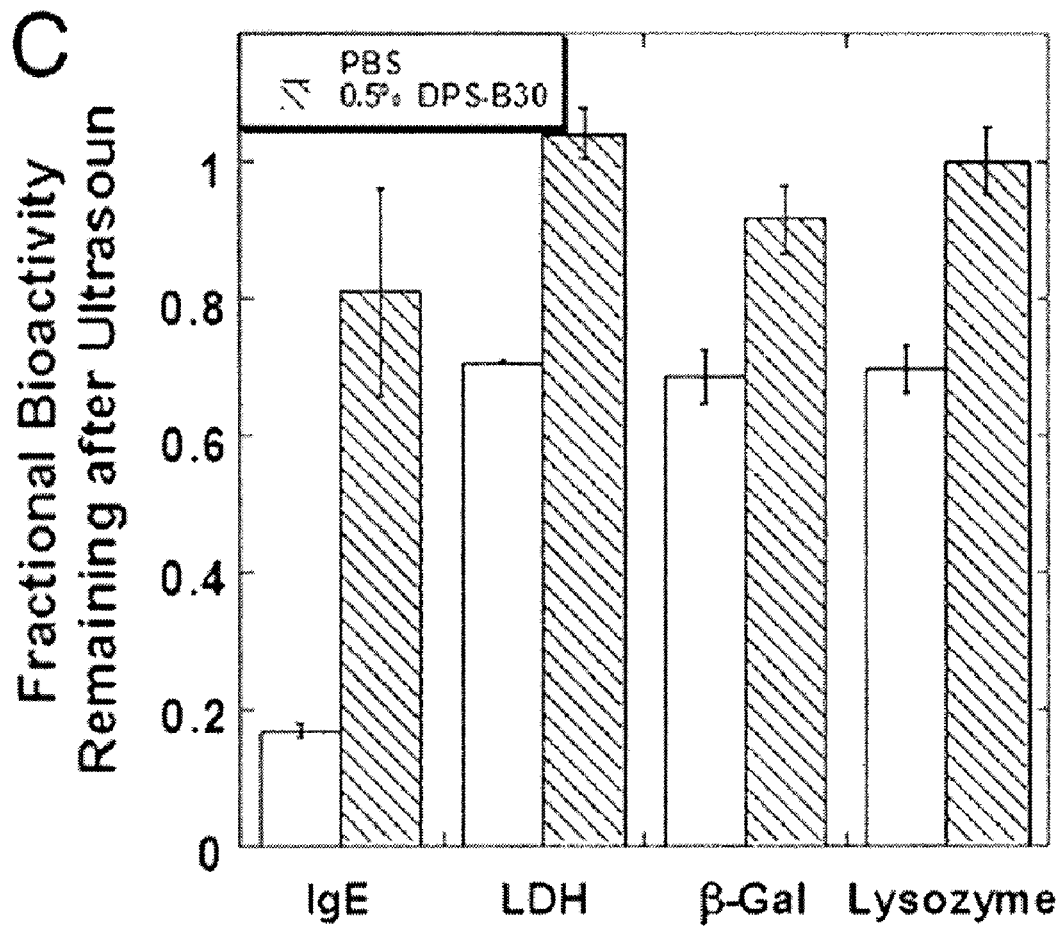
FIG. 2c illustrates a comparison of the effect on bioactivity of IgE, LDH, β-gal, and lysozyme when the proteins were subjected to ultrasonic denaturing stress using DPS-B30 (0.5% (w/v)) as a solubilizing composition versus using PBS.

As shown in FIG. 2c, preservation of fractional bioactivity for IgE, LDH, β-Gal, and lysozyme proteins, when prepared in DPS-B30 formulation, was observed. Significant loss of bioactivity was observed for proteins prepared in PBS (open bars).

Example 5

Allergic Mouse Model

Allergy biomarkers (IgE antibodies) were extracted from eczematic skin and facilitated diagnosis of allergic dermatitis. Six to eight week old female BALB/CJ mice were purchased from Charles River Labs (Wilmington, Mass.) and maintained under pathogen-free conditions. All procedures performed on the mice were approved by the Institutional Animal Care and Use Committee of University of California, Santa Barbara, Calif. Allergic reaction was induced in mice by an epicutaneous exposure protocol. After anesthesia with 1.25-4% isofluorane in oxygen, the skin on the back of the mice was shaved and then tape stripped ten times by a 3M tape (3M Health Care, St Paul, Minn.) to introduce a standardized skin injury. A gauze patch (1 cm×1 cm) soaked with 100 μL of 0.1% OVA was placed on the back skin and secured with a breathable elastic cloth-based adhesive tape. The patches were kept affixed for 1 week. The whole experiment comprised a total of three 1-week exposures with a 2-week interval between each exposure week. A flanged chamber (skin exposure area of 1.33 cm$^2$) was glued to the shaven skin area with a minimal amount of cyanoacrylate-based adhesive. The chamber was filled with 1.8 ml of 0.5% DPS-B30 surfactant formulation and ultrasound was applied according to the operating parameters describe above. Skin biopsies of ultrasound treated or untreated eczema skin sites were obtained.

Figure 3:
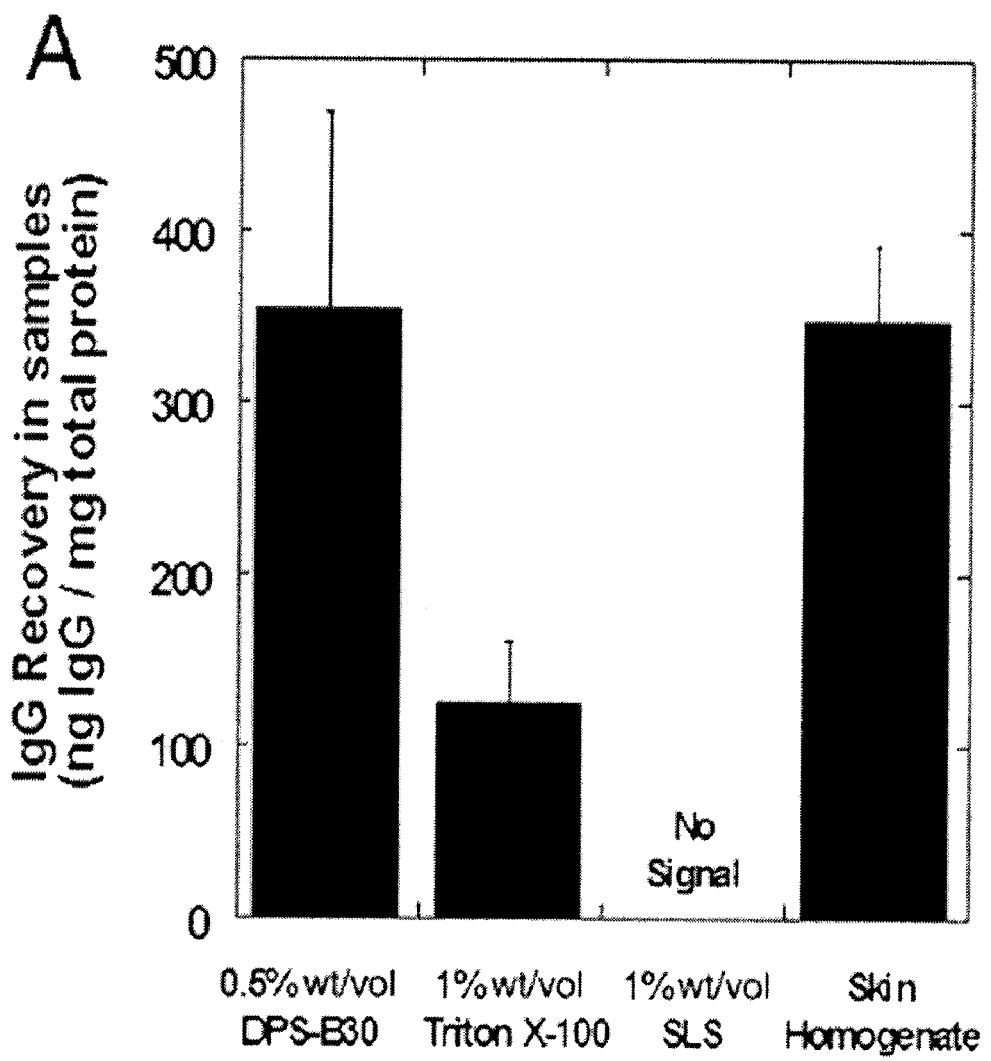
FIG. 3 illustrates a comparison of IgG recovery from mouse skin using various solubilizing compositions.

FIG. 3 illustrates that the extracted samples contained about a three-fold higher amount of IgE antibodies in allergic skin than healthy mouse skin. Consistent with the pathology of allergic disease, no statistically significant difference was found between the amounts of IgG antibodies in the samples obtained from allergic and healthy mice skin using 0.5% DPS-B30 surfactant formulation and ultrasound.

Example 6

Profiling and Quantification of Lipids

In addition to proteins, it was assessed whether the application of DPS-B30 and ultrasound can efficiently sample a multitude of lipids from tissues. Samples were prepared in vitro from excised porcine skin and mucosal tissues including colon, nasal, and buccal mucosa. Tissues were mounted on a Franz diffusion cell assembly and subjected to 3 min in situ sonication. Tissue homogenate samples were also prepared for comparative analysis. Lipids from each sample were extracted using the Bligh-Dyer method. After evaporating the solvent under a stream of nitrogen, lipid weight was estimated, and the lipids were reconstituted in 250 µL of chloroform/methanol (2:1) solvent for thin layer chromatography ("TLC") analysis. 10 cm long aluminum-backed TLC plates coated with a 200 µm-thick layer of silica gel (60 Å) (Merck-5554/7, EMD Chemicals, Gibbstown, N.J.) were washed with chloroform/methanol (2:1), air dried, and 20 µL of each lipid extract was applied at 1 cm distance from the bottom of the plate. The chromatograms were developed successively with hexane (to 9 cm), toluene (to 9 cm), and hexane/ether/acetic acid (70:30:1, twice to 5 cm). Cholesteryl stearate (cholesteryl esters, "CE"), triolein (triglycerides, "TG"), oleic acid (free fatty acids, "FA"), lanosterol ("LA"), and cholesterol ("CH") were spotted on TLC plates as reference standards. Lipids on the chromatographs were probed by charring with 8% $H_3PO_4$ solution containing 10% w/v $CuSO_4$ and 5% v/v methanol, followed by slow heating at 180° C. in an oven until a good contrast was obtained.

Figure 4A:
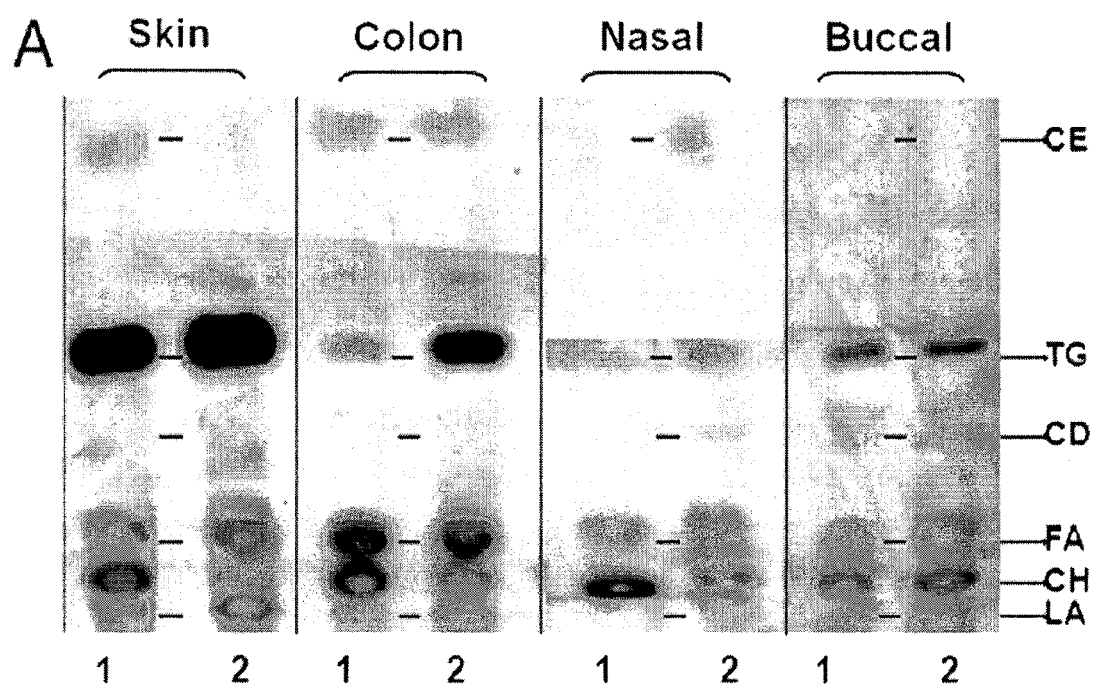
FIG. 4a illustrates a comparison of non-polar lipids extracted from porcine skin and mucosal tissues using DPS-B30 (lane 2), with the lipid profiles in tissue homogenate samples (lane 1).
Figure 4B:
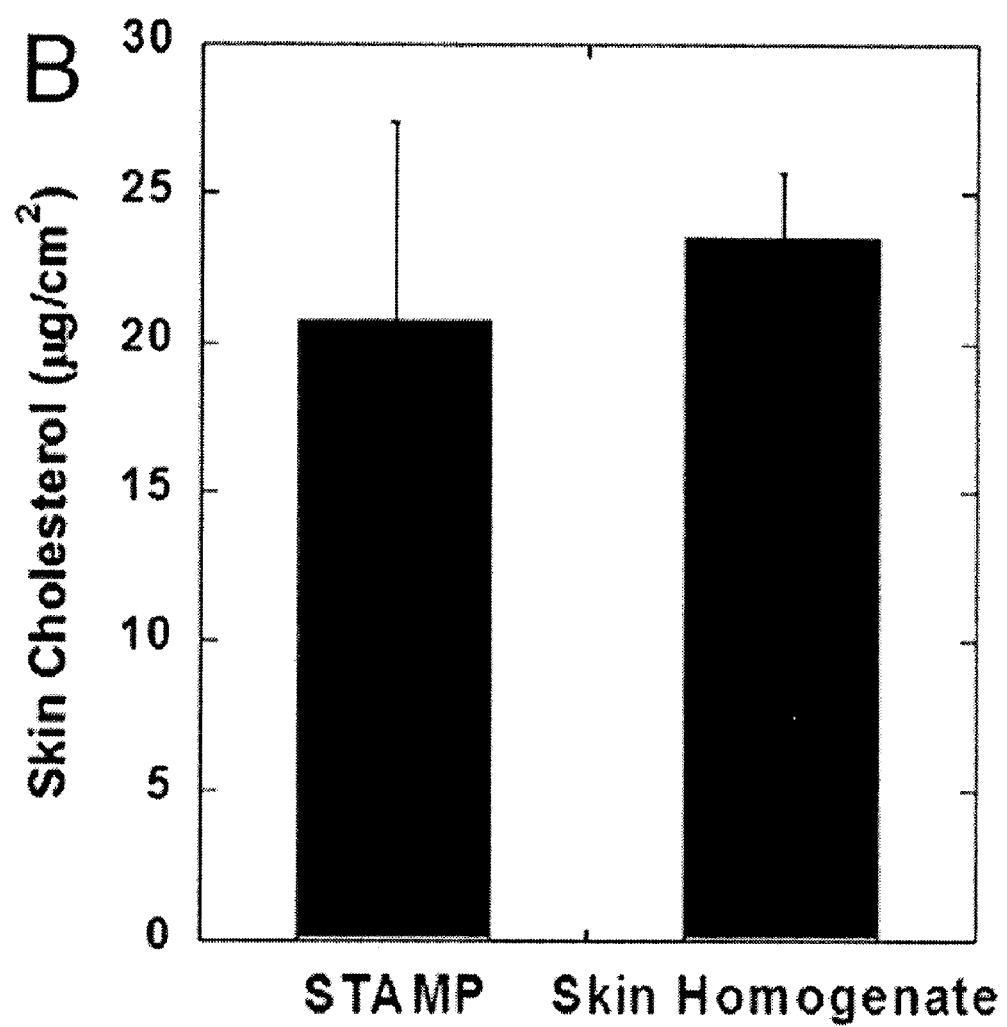
FIG. 4b illustrates a comparison of the results of in vivo sampling of mouse skin for cholesterol sampled using DPS-B30 and ultrasonic applied energy, with the actual amount of cholesterol natively present in the skin.

The chromatographs in FIG. 4a illustrate that DPS-B30 (lane 2) was able to retrieve all major types of non-polar lipids from porcine skin and mucosal tissues in vitro, which compared well with the lipid profiles in tissue homogenate samples (lane 1). Six types of lipids were sampled: CE, TG, cholesteryl diesters (CD), FA, CH, and LA. The sampling efficiency was further quantified in vivo using mice. In vivo sampling of mouse skin showed that the amount of cholesterol sampled from skin using ultrasound and DPS-B30 was representative of the actual amount of cholesterol natively present in skin (FIG. 4b). Since cholesterol quantification necessitated structural integrity and chemical stability of the cholesterol molecule, it may be inferred that DPS-B30 and applied energy effectively sampled, and preserved, the functionality of cholesterol.

Example 7

Sampling of Genomic DNA

Samples were prepared from excised porcine skin using 0.5% (w/v) DPS-B30 surfactant formulation and a brief in situ 3 min sonication. Skin was mounted on a Franz diffusion cell assembly. As a comparative control, samples were obtained by swabbing the skin with cotton swabs (B4320115, BD Diagnostics, Franklin Lakes, N.J.). A sterile metal ring (area of 3.3 cm$^2$) was clamped onto the skin surface and sampling was restricted by swabbing skin enclosed within the ring. Swabs were soaked in sterile PBS and gently rubbed against the skin surface for 20 seconds. Each swab was extracted with 1 mL PBS solution for 1 h. Samples were also obtained by scraping skin. A sterile metal ring was firmly held against the skin surface and 1 mL of 0.1% (w/v) Triton X-100 in 0.075 M phosphate buffer, pH 7.9, was dispensed onto the skin surface. The skin surface within the ring was rubbed firmly for 1 min with a Teflon cell scraper and the resulting sample was collected. The procedure was repeated at the same skin site for two additional times and the samples were pooled together. Bacterial genome was purified from each sample by standard phenol-chloroform extraction method. The samples were first incubated in a solution comprising 20 mM Tris at pH 8.0 (BP154, Fisher Scientific, Fairlawn, N.J.), 2 mM EDTA (BP120, Fisher Scientific), 1.2% Triton X-100 (BP151-100, Fisher Scientific), and 20 mg/mL lysozyme (62970, Sigma Aldrich, St. Louis, Mo.) for 30 min at 37° C. Samples were incubated for 3 hours at 37° C. in a solution comprising 0.1 mg/mL Proteinase K (P2308, Sigma-Aldrich), 0.5% (w/v) sodium lauryl sulfate (S529, Fisher Scientific), and 100 mM sodium chloride (BP358, Fisher Scientific). Genomic DNA was extracted with an equal volume of phenol (P4557, Sigma-Aldrich), followed by extraction with phenol/chloroform/isoamyl alcohol, 25:24:1 (P2069, Sigma-Aldrich). The DNA was precipitated by incubation with ethanol and centrifugation for 20 min. The DNA pellets were washed twice with 70% ethanol, allowed to dry, and re-suspended in 80 µL of tris buffer. To quantify the amount of bacteria in each sample, real-time quantitative PCR was performed based on an amplicon of the conserved 16S rRNA bacterial gene. Analysis of the 16S gene was performed on the iCycler PCR machine (Bio-Rad Laboratories, Hercules, Calif.) using optical grade 96-well plates. Bacterial 16S gene was amplified using forward primer 63F (5'-22 AGAGTTTGATCCTGGCTCAG-3') and reverse primer 355R (5'-GACGGGCGGTGTGTRCA-3 35,41). For each sample, 10 µL of purified genomic DNA was mixed with 2 pmol of each primer and Platinum PCR Supermix (11784, Invitrogen, Carlsbad, Calif.) to a final reaction volume of 20 µL. Thermal cycling was set as follows: Initial denaturation at 94° C. for 5 min, followed by 32 cycles of a 30 sec 94° C. denaturation, 30 sec annealing at 66° C., and 30 sec elongation at 72° C., all followed by a final extension of 10 min at 72° C. To calibrate the number of bacteria in each sample, a standard curve was constructed by amplifying serial dilutions of genomic DNA from known quantities of *E. Coli* cells in 10 µL of tris buffer.

Additional experiments were conducted to evaluate the structural integrity of bacterial DNA under sonication stress. Bacterial culture of *E. Coli* strain DH10α (18290-015, Invitrogen) were grown in Luria-Bertani (BP1426, Fisher Scientific) at 37° C., 250 rpm. *E. Coli* cells were quantified with a spectrophotometer (Biophotometer, Eppendorf, Hauppauge, N.Y.), and a bacterial culture of 0.25×10$^9$ cells/mL was considered to correspond to an optical density absorbance value of 0.25 at a wavelength of 600 nm. Culture was harvested by centrifugation and the resulting pellet was suspended in either tris buffer (10 mM Tris-HCl, pH 7.9) or 0.5% (w/v) DPS-B30 surfactant formulation at a concentration of 10$^9$ cells/mL. One mL of cell suspension was placed in a sterilized sonication chamber (centrifuge tube #430290, Corning Inc., Corning, N.Y.). Sonication (20 kHz, 2.4 W/cm$^2$, 50% duty cycle, 3 min) was performed by lowering the probe transducer to a distance of 5 mm from the bottom of the chamber. After sonication, genome DNA was purified from each sample using the DNeasy DNA Extraction Kit (69504, Qiagen, Valencia, Calif.). The purified genomic DNA was re-suspended in 400 µL of Buffer AE and subjected to electrophoresis for 90 min at 100 V in a 2% (w/v) Tris-acetate-EDTA-agarose gel. The gels were stained with SYBR Gold (S11494, Invitrogen) and visualized under UV light.

Figure 4C:
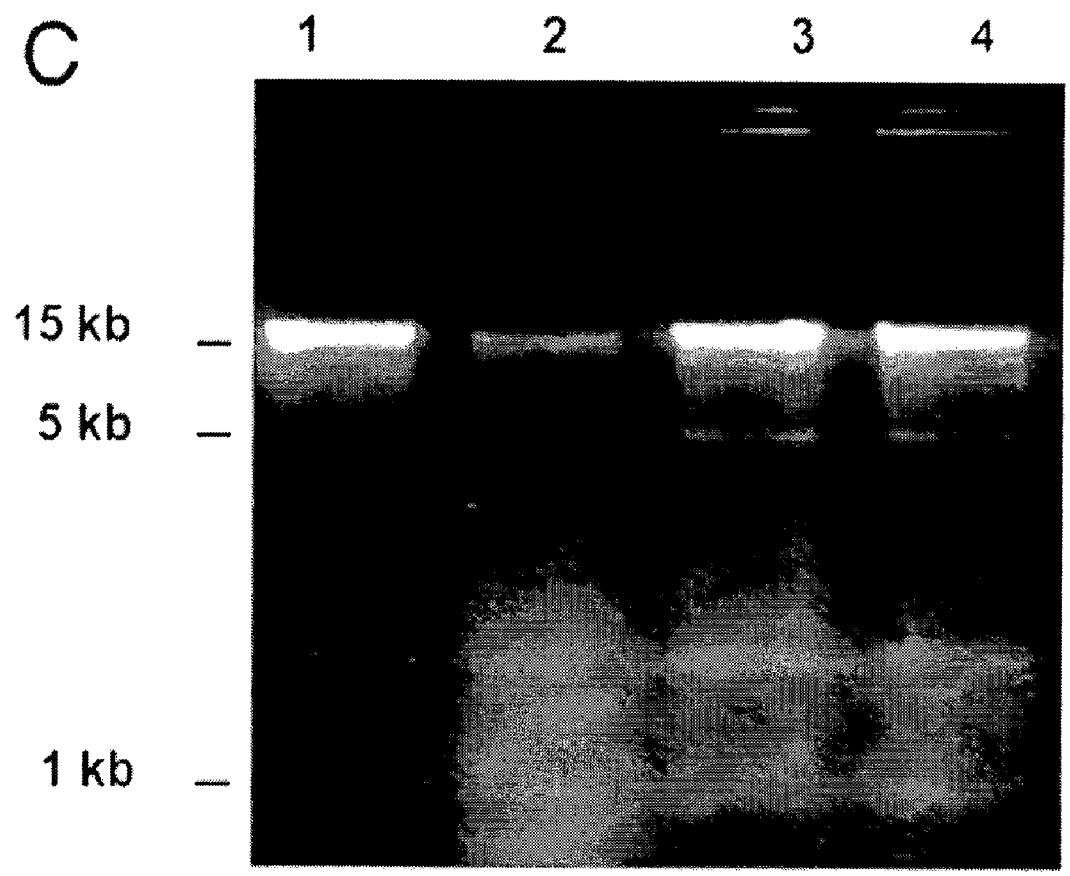
FIG. 4c illustrates the effect of sonication on bacterial DNA prepared in TBS (lane 2) compared to non-sonicated bacterial suspension in TBS (lane 1), non-sonicated bacterial suspension in DPS-B30 (lane 3), and sonicated bacterial suspension in DPS-B30 (lane 4).

FIG. 4c illustrates that sonication significantly damaged bacterial DNA prepared in TBS (lane 2) compared to non-sonicated bacterial suspension in TBS (lane 1) or in DPS-B30 (lane 3). In contrast, DPS-B30 surfactant formulation (lane 4), when added to the bacterial suspension, provided outstanding protection to DNA's structural integrity from denaturing stress of the sonication procedure. This is consistent with preservation of the bioactivity of proteins with DPS-B30 formulation (FIG. 2c).

Example 8

Localized Transport Regions

Figure 5A:
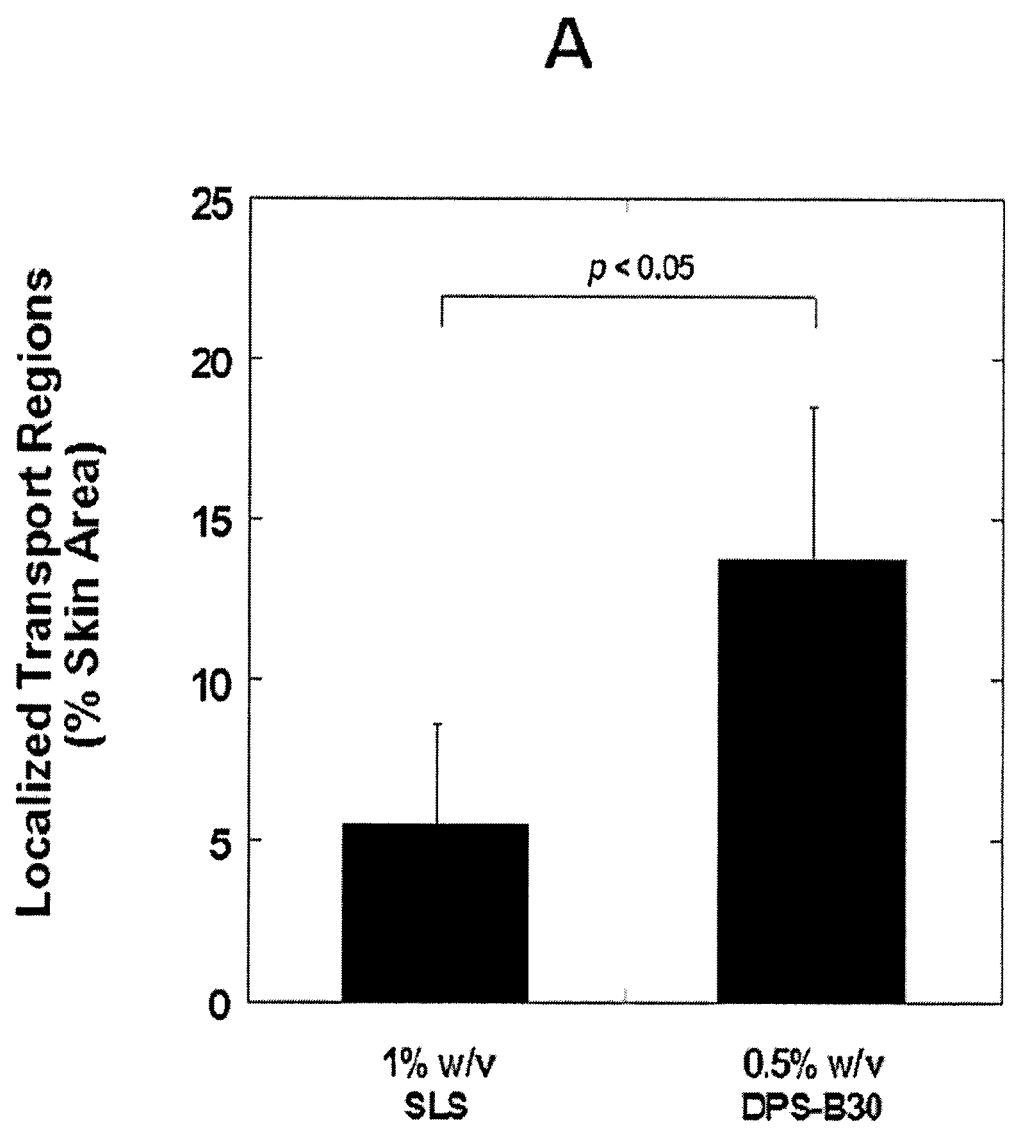
FIG. 5a illustrates a comparison of the localized transport region ("LTR") area of skin treated with ultrasound and 0.5% (w/v) DPS-B30, with the LTR area of skin treated with ultrasound and 1% (w/v) SLS.
Figure 5B:
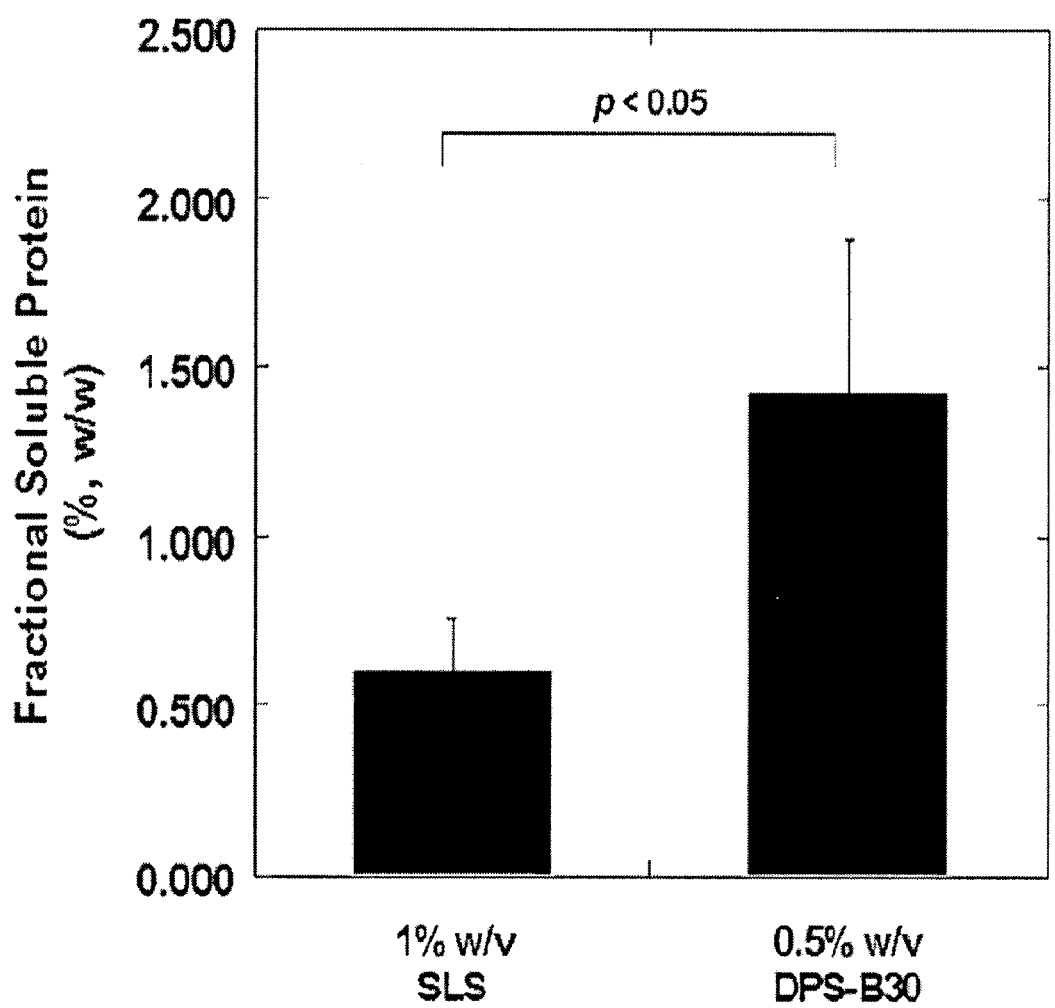
FIG. 5b illustrates a comparison of the proportion of soluble protein in a sample of skin treated with ultrasound and 0.5% (w/v) DPS-B30, with the proportion of soluble protein in a sample of skin treated with ultrasound and 1% (w/v) SLS.

Increased sampling of functional tissue constituents as described herein is a compounded result of the unique and unexpected ability of DPS-B30 to solubilize molecules from tough tissue assemblies, as well as to retain molecular bioactivity despite applied energy, such as sonication stress. The effect of surfactant and applied energy on skin, however, is highly localized, leading to the formation of LTRs. Application of ultrasound to skin with 0.5% (w/v) DPS-B30 may lead to at least a 3-fold enhancement of area of LTRs compared to that from 1% (w/v) SLS (FIG. 5a). Additionally, DPS-B30-ultrasound combination yielded about a 3-fold higher proportion of soluble protein in the sample compared to that yielded by SLS-ultrasound combination (FIG. 5b). Collectively, these results indicate that for a given ultrasound condition, DPS-B30 formulation provides dramatically and unexpectedly higher recovery of solubilized protein compared to that by SLS.

Figure 6A:
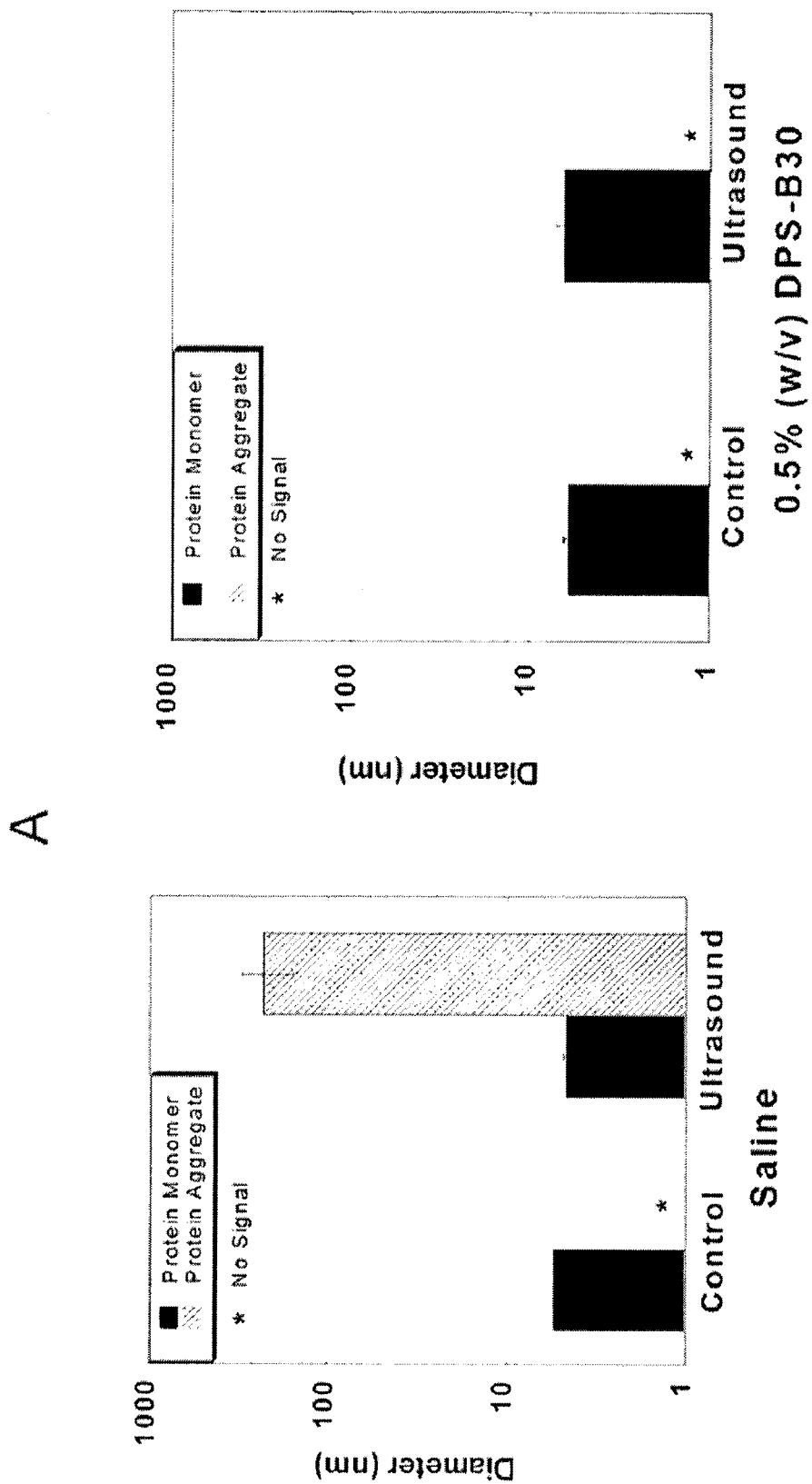
FIG. 6a illustrates a comparison of the diameter of lysozyme that has been solubilized in saline and subjected to ultrasound, with lysozyme that has been solubilized in 0.5% (w/v) DPS-B30 and subjected to ultrasound.
Figure 6B:
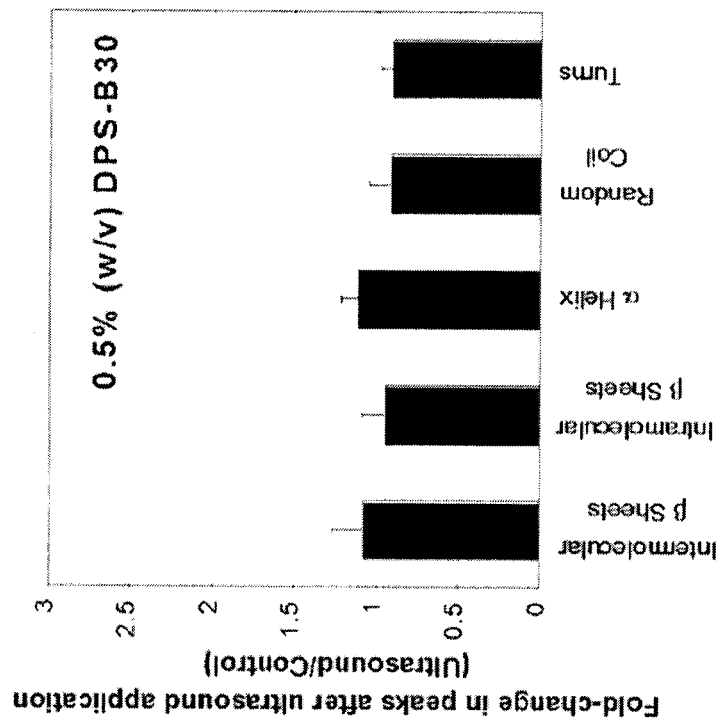
FIG. 6b illustrates a comparison of the rearrangement of β-sheets (from intramolecular to intermolecular β-sheets) observed after sonication of lysozyme prepared in saline, with the rearrangement observed after sonication of lysozyme prepared in 0.5% (w/v) DPS-B30.
Figure 6B:
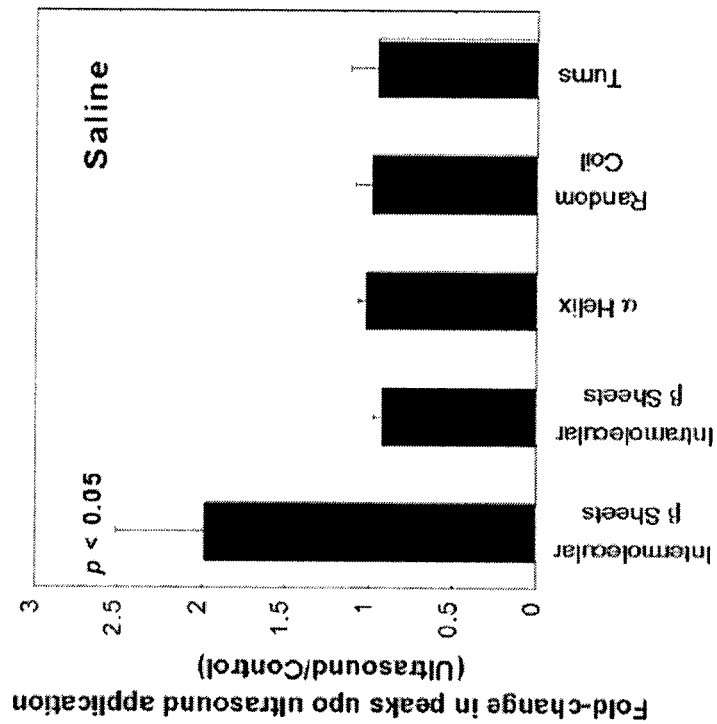

The benefits of DPS-B30 are further escalated by its ability to preserve the protein structure. Unlike SLS, DPS-B30 prevents protein denaturation on its own. In addition, DPS-B30 protects proteins against ultrasound-induced denaturation. Dynamic light scattering and FT-IR spectroscopy studies were performed to obtain insight into this behavior. Lysozyme was used as a model protein because of its availability in pure and large quantities, and its well-characterized behavior in aqueous solution. Light scattering studies revealed that lysozyme, when solubilized in saline, rapidly forms large aggregates when subjected to ultrasound (aggregate size of 229.5±72 nm compared to native size of 5.4±0.01 nm; FIG. 6a). In contrast, lysozyme prepared in 0.5% (w/v) DPS-B30 surfactant formulation did not aggregate when exposed to ultrasound. Direct measurement of lysozyme bioactivity and FT-IR studies (FIG. 6b) confirmed these findings. A significant rearrangement of β-sheets (from intramolecular to intermolecular β-sheets) was observed after sonication of lysozyme prepared in saline. Increased content of intermolecular β-sheets is the most prominent change in the secondary structure of aggregated proteins and is commonly found in proteins subjected to thermal, chemical, or physical stress. Rearrangement of β-sheets to intermolecular conformation without grossly changing the secondary protein structure is expected. Physical shearing, similar to cavitation-induced forces experienced by protein under ultrasound exposure, has been shown to disrupt protein's native fold, but leave secondary structural elements intact and thereby enhance intermolecular interactions and aggregation. Notably, formation of aggregates and increase in the intermolecular β-sheets for several proteins (including lysozyme) subjected to low-frequency ultrasound have been reported. Consistent with the absence of aggregates (found by light scattering), no change in the intermolecular β-sheet content was observed when DPS-B30 surfactant formulation was added during sonication of lysozyme (FIG. 6b). These results demonstrate the ability of DPS-B30 to prevent protein aggregation.

The above Examples illustrate that the compositions described herein may provide at least three unexpected and surprising results: (1) biomolecular recovery from larger skin area; (2) higher fraction of solubilized proteins; and (3) protection of proteins against denaturation.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See Bryan A. Garner, A Dictionary of Modern Legal Usage 624 (2d. Ed. 1995). Also, to the extent that the terms "in" or "into" are used in the specification or the claims, it is intended to additionally mean "on" or "onto." Finally, where the term "about" is used in conjunction with a number, it is intended to include ±10% of the number. In other words, "about 10" may mean from 9 to 11.

As stated above, while the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Therefore, the application, in its broader aspects, is not limited to the specific details, illustrative examples shown, or any apparatus referred to. Departures may be made from such details, examples, and apparatuses without departing from the spirit or scope of the general inventive concept.

What is claimed is:

1. A composition, comprising:
   3-(decyl dimethyl ammonio) propane sulfonate; and
   tetraethylene glycol dodecyl ether.

2. The composition of claim 1, wherein the 3-(decyl dimethyl ammonio) propane sulfonate and the tetraethylene glycol dodecyl ether are present in a total concentration of about 0.5% (w/v) in a buffer solution.

3. The composition of claim 1, wherein the 3-(decyl dimethyl ammonio) propane sulfonate and the tetraethylene glycol dodecyl ether are present in a total concentration of from about 0.01% (w/v) to about 5% (w/v) in a buffer solution.

4. The composition of claim 1, wherein the 3-(decyl dimethyl ammonio) propane sulfonate and the tetraethylene glycol dodecyl ether are present in a ratio of from about 3:2 to about 2:3.

5. The composition of claim 1, wherein the composition is exclusive of at least one of polyoxyethylene sorbitans combined with fatty acids, cationic surfactants, sorbitans, and sodium alkyl sulfates.

6. The composition of claim 1, wherein the composition has a pH more basic than 7.0.

7. The composition of claim 1, wherein the composition has a pH of between 7.0 and 9.0.

8. A method for solubilizing a region of interest on skin, comprising:
   applying energy to the region of interest; and
   contacting the region of interest with a composition,
      wherein the composition comprises:
         3-(decyl dimethyl ammonio) propane sulfonate; and
         a polyethylene glycol dodecyl ether.

9. The method of claim 8, wherein the applying energy comprises applying mechanical energy.

10. The method of claim 8, wherein the region of interest comprises a precancerous condition selected from one or more of actinic keratosis, leukoplakia, Barretts esophagus, and right-colon pre-cancer plaque, and a surface cancer arising from the precancerous condition.

11. The method of claim 8, wherein the region of interest comprises at least one of hardened skin and hyperkaratanized skin.

12. The method of claim 8, wherein the region of interest comprises at least one of necrotic eschar and fibrinous slough.

13. The method of claim 8, wherein the region of interest comprises at least one of age spots, skin tags, seborrheic keratosis, scar tissues, xanthomas, non-cancerous hyperproliferative tissue, surface bumps, and scaly patches.

14. The method of claim 8, further comprising:
    removing at least a portion of the solubilized region of interest to leave an exposed area on the skin; and
    applying to the exposed area at least one of a therapeutic composition and a cosmetic composition.

15. The method of claim 14, wherein the therapeutic composition comprises at least one of a DNA-based drug, an RNA-based drug, a protein-based drug, a peptide-based drug, a lipid-based drug, a carbohydrate-based drug, a small molecule drug, a nanoparticle-based drug, and a liposome-encapsulated drug.

16. The method of claim 14, wherein the cosmetic composition comprises at least one of elastin, an elastin-based peptide, collagen, a collegen-based peptide, resveratrol, idebenone, co-enzyme Q10, acetyl hexapeptide-3, glycosaminoglycans, palmitoyl pentapeptide-4, sodium hyaluronate, and combinations thereof.

17. The method of claim 8, wherein the polyethylene glycol dodecyl ether comprises tetraethylene glycol dodecyl ether.

18. A method for recovering analytes from mucosal membrane, skin, or other tissue, comprising:
    applying energy to a region of interest on the mucosal membrane, skin, or other tissue containing at least one analyte;
    contacting the region of interest with a tissue solubilizing composition, thereby solubilizing at least some of the region of interest; and
    collecting the at least one analyte from the solubilized region of interest,
    wherein the composition comprises:
       3-(decyl dimethyl ammonio) propane sulfonate; and
       a polyethylene glycol dodecyl ether.

19. The method of claim 18, wherein the applying energy comprises applying mechanical energy.

20. The method of claim 18, wherein the analyte comprises a protein.

21. The method of claim 18, wherein the analyte comprises a cancer biomarker.

22. The method of claim 18, wherein the analyte comprises an antibody.

23. The method of claim 18, wherein the analyte comprises a peptide.

24. The method of claim 18, wherein the analyte comprises a lipid.

25. The method of claim 18, wherein the analyte comprises a nucleic acid.

26. The method of claim 18, wherein the analyte comprises a small molecule.

27. The method of claim 18, wherein the analyte comprises a microbe.

28. The method of claim 18, wherein the analyte comprises a warfare agent.

29. The method of claim 18, wherein the analyte comprises an environmental contaminant.

30. The method of claim 18, wherein the analyte comprises a drug.

31. The method of claim 18, wherein the polyethylene glycol dodecyl ether comprises tetraethylene glycol dodecyl ether.

* * * * *